(12) United States Patent
Li et al.

(10) Patent No.: US 7,397,554 B1
(45) Date of Patent: Jul. 8, 2008

(54) APPARATUS AND METHOD FOR EXAMINING A DISK-SHAPED SAMPLE ON AN X-Y-THETA STAGE

(75) Inventors: Guoguang Li, Fremont, CA (US); Marc Aho, Mountain View, CA (US)

(73) Assignee: n&k Technology, Inc., San Jose, CA (US)

( * ) Notice: Subject to any disclaimer, the term of this patent is extended or adjusted under 35 U.S.C. 154(b) by 300 days.

(21) Appl. No.: 11/325,029

(22) Filed: Jan. 4, 2006

(51) Int. Cl.
*G01N 21/00* (2006.01)
(52) U.S. Cl. ............... 356/237.2; 356/237.1; 356/237.5
(58) Field of Classification Search ... 356/237.1–237.5, 356/608, 614, 401; 250/208.1, 208.3; 382/145
See application file for complete search history.

(56) References Cited

U.S. PATENT DOCUMENTS

| | | | |
|---|---|---|---|
| 3,147,474 A | 9/1964 | Kliman | |
| 4,669,866 A * | 6/1987 | Phillips | ........................ 355/43 |
| 4,676,649 A * | 6/1987 | Phillips | ...................... 356/401 |
| 5,513,948 A | 5/1996 | Bacchi | |
| 5,760,906 A * | 6/1998 | Sato | ........................... 356/602 |
| 5,852,413 A | 12/1998 | Bacchi | |
| 5,936,726 A * | 8/1999 | Takeda et al. | ............. 356/237.2 |
| 5,990,650 A | 11/1999 | Brock | |
| 6,275,742 B1 | 8/2001 | Sagues | |
| 6,320,609 B1 | 11/2001 | Buchanon | |
| 6,426,502 B1 | 7/2002 | Finarov | |
| 6,507,394 B1 | 1/2003 | Cheng | |
| 6,747,746 B2 | 6/2004 | Chizhov | |
| 6,778,273 B2 | 8/2004 | Norton | |
| 6,836,690 B1 | 12/2004 | Spady | |
| 6,882,413 B2 | 4/2005 | Bowman | |
| 7,110,106 B2 * | 9/2006 | Xu et al. | ................... 356/237.5 |
| 7,127,098 B2 * | 10/2006 | Shimoda et al. | ............. 382/145 |
| 2002/0042153 A1 | 4/2002 | Holcman et al. | ............... 438/14 |
| 2003/0020912 A1 | 1/2003 | Norton et al. | ................ 356/369 |
| 2003/0030806 A1 | 2/2003 | Ebert et al. | .................. 356/369 |

FOREIGN PATENT DOCUMENTS

EP    0971254    12/2000

* cited by examiner

*Primary Examiner*—Sang Nguyen
(74) *Attorney, Agent, or Firm*—Lumen Patent Firm, Inc.

(57) ABSTRACT

An apparatus and method for examining features of a planar, disk-shaped samples on a stage that holdings the sample and has an X-drive, a Y-drive and a θ-drive for rotating the stage about a center of rotation defined in the stage coordinates. The sample is placed on the stage such that the center of the sample is substantially aligned with the center of rotation and a measurement assembly is located above the sample to examine the features optically. A scheduling module coordinates the X-drive, the Y-drive and the θ-drive with the measurement assembly such that the sample is examined in an even number n of angular sectors defined by a sector angle Θ that is the same for each sector. Specifically, the sector angle Θ is defined in terms of n as follows:

$$\Theta = \frac{360°}{n},$$

where $n=4m$ and m is an integer, such that a multiple of sector angle Θ always includes angles 90° and 180°.

23 Claims, 7 Drawing Sheets

APPARATUS AND METHOD FOR EXAMINING A DISK-SHAPED SAMPLE ON AN X-Y-THETA STAGE

FIELD OF THE INVENTION

This invention relates generally to an apparatus for optically examining a disk-shaped sample placed on a stage capable of linear motion along the X and Y directions and rotation by an angle θ about a center of rotation.

BACKGROUND ART

The field of test and measurement spans a wide range of apparatus and techniques that include stages designed for accurate positioning and moving of samples under test. More specifically, the field of optical metrology requires stages that are capable of moving samples in a way that is accurate, reproducible and allows the inspection of the entire surface area of the sample. In other words, the stage needs to allow the optical inspection mechanism to access with its probe beam any surface portion of the sample. This is particularly important in samples that are disk-shaped, such as semiconductor wafers, whose features are being examined or inspected prior to dicing or cutting the wafer into individual circuit dies.

The prior art teaches a number of stages for retaining and moving samples, such as wafers for optical inspection. For example, U.S. Pat. No. 6,320,609 teaches an R-θ stage and assumes that the center of rotation of the polar coordinate stage can be made coincident with the center of measurement beam spot (or the center of the field of view of the imaging system). In practice, there is always some offset between these two centers. This means that there is an area, i.e., a blind spot that cannot be placed under the beam spot by an R-θ stage. In addition, when grating structures on a wafer are measured at oblique incidence of the test beam, the grating orientation relative to the direction of incidence varies from location to location, because the wafer will typically rotate as it moves. This is a serious problem for optical scatterometry measurements.

To overcome this problem, U.S. Pat. No. 6,882,413 teaches a very complicated optical setup. The setup is configured to move the optical assembly in a manner similar to the way in which rotation is compensated. Unfortunately, due to the small amounts of rotation, or even continuous rotation, the apparatus taught in this reference suffers from loss of angular resolution. Furthermore, misalignments in wafer positioning cause a blind spot that cannot be examined. A similar problem affects a system for measuring periodic structures, as disclosed in U.S. Pat. No. 6,721,052 by Zhao et al. Here the inventors are studying a periodic structure by illuminating it by polychromatic electromagnetic radiation and collecting radiation from the structure in two different polarizations. To reduce the footprint of the system, the measurement instrument and the wafer bearing the periodic structure are both moved. For example, they both undergo translational and rotational motion in such a way that the illumination beam from the apparatus scans a spiral path on the wafer. Thus, the system incurs the problems associated with continuous rotation as discussed above.

In fact, none of the above approaches offer a simple and effective apparatus and method for examining disk-shaped samples such as semiconductor wafers with a small footprint stage that is not susceptible to blind spots and issues associated with low angular resolution.

OBJECTS AND ADVANTAGES

In view of the above prior art limitations, it is an object of the invention to provide an apparatus and method for examining planar, disk-shaped samples in a small footprint apparatus that is insensitive to misalignments and problems associated with low angular resolution. In particular, the apparatus is intended to be able to operate within the footprint of the sample only while still being able to efficiently examine the entire surface of the sample.

It is a further object of the invention to provide an apparatus that can examine samples such as semiconductor wafers in a configuration that allows the measurement assembly to travel in a very flat and precise manner.

These and other objects and advantages of the invention will become apparent from the ensuing description.

SUMMARY OF THE INVENTION

The objects and advantages of the invention are addressed by an apparatus for examining the features of a disk-shaped sample. The sample can be any generally planar and disk-shaped object bearing features, especially microscopic ones, and in some particular cases it can be a semiconductor wafer. The apparatus has a stage for holding or supporting the sample. An X-drive and a Y-drive are provided for moving the stage along an $X_s$ direction and a $Y_s$ direction defined in the stage coordinates, respectively. The apparatus also has a θ-drive for rotating the stage about a center of rotation defined in the stage coordinates. The sample is placed on the stage such that the center of the sample is substantially aligned with the center of rotation. If necessary, pre-alignment procedures are used to ensure proper placement of the sample on the stage.

The apparatus has a measurement assembly located above the sample. The measurement assembly is usually designed to examine the features of the sample optically. Such measurement is commonly performed by illuminating the sample with test or probe radiation, and studying a scattered radiation returning from the sample. In accordance with the invention, the apparatus is equipped with a scheduling module for coordinating the X-drive, the Y-drive and the θ-drive with the measurement assembly such that the sample is examined in an even number n of angular sectors. The angular sectors are defined by a sector angle Θ that is the same for each sector. Specifically, the sector angle Θ is defined in terms of n as follows:

$$\Theta = \frac{360°}{n};$$

where n=4m and m is an integer, such that multiple rotations of sector angle Θ always includes angles 90° and 180°.

In a preferred embodiment of the invention, the apparatus is also equipped with an image rotation module for rotating an image of a selected asymmetric reference feature identified on the sample. This image can be reconstructed from the scattered radiation in the field of view of the measurement assembly or it can be obtained independently with separate elements. A pattern matching module uses the image of the reference feature to perform a matching of the image of the reference feature with a stored image of the reference feature at the various possible values rotation angle θ. Preferably, the reference feature exhibits a sufficient level of asymmetry to distinguish a number of feature orientations at least equal to the number n.

The pattern matching performed with the aid of the image rotation module and the pattern matching module finds many uses in the apparatus of invention. In one embodiment, the apparatus has a drive feedback that is in communication with the pattern matching module. Based on matching the actual image with the stored reference feature the drive feedback controls at least one of the drives, i.e., X-drive, Y-drive and θ-drive, but preferably at least the θ-drive. In another embodiment, the apparatus has an angular sector identification module that is connected to the pattern matching module. The identification module identifies the angular sectors based on the pattern matching. In still another embodiment, the apparatus has a sample offset correction module that is in communication with the pattern matching module and performs offset correction of the sample based on the pattern matching. In any of these applications of the pattern matching module, as well as any other applications thereof, it is advantageous to ensure a corresponding level of asymmetry of the stored reference feature to ensure that the requisite angular resolution is obtained.

In addition to determining rotation angle θ, it is sometimes important to properly orient the measurement assembly with respect to the features that are to be examined in any given sector. A calibration pattern consisting of features to be examined can be used for this purpose. Specifically, the measurement assembly can be oriented with respect to the calibration pattern prior to commencing examination.

In some applications, the θ-drive has a stepper for rotating the sample by angular steps that are equal to the sector angle Θ. Any suitable mechanism can be used to enforce such step-wise rotation, including hard stops. In any of these applications the measurement assembly itself can be stationary or mobile. In the event it is mobile, it may also have hard stops for controlling its angular movement by increments equal to the sector angle Θ.

The invention further encompasses a method for examining features of a sample, e.g., a semiconductor wafer that is placed on a stage with three degrees of freedom of motion. Specifically, the method is practiced on a stage with an $X_s$ direction of motion, a $Y_s$ direction of motion and a θ rotation.

The sample is placed on the stage such that its center is aligned with the center of rotation. The sample is also partitioned or subdivided into an even number n of angular sectors defined by sector angle Θ. Preferably, the sector angle Θ is selected from the following three angles: 90°, 45° and 22.5°. Note that smaller sector angles Θ are also possible, but may not be preferred due to the increased angular resolution required when implementing pattern matching for feedback and control of the drives, sector identification or correction of sample offset.

The method of invention can be practiced in many variants. In some a specific schedule of examination of the angular sectors can be implemented. For example, the schedule may dictate consecutive examination of diametrically opposite pairs of angular sectors.

A detailed description of the preferred embodiments of the invention is presented below in reference to the appended drawing figures.

DETAILED DESCRIPTION

Figure 1:
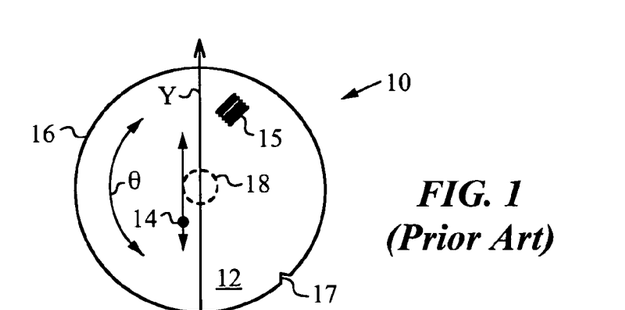
FIG. 1 (prior art) is a top plan view illustrating the limitation of the R-θ stage.

The present invention and its principles will be best understood by first reviewing the limitations of a prior art R-θ stage 10 as shown in FIG. 1. Stage 10 is designed for optically examining a disk-shaped object 12, e.g., a semiconductor wafer. During examination wafer 12 rotates over angle θ and is illuminated by a measurement beam spot 14 from an optical examination device (not shown). The examination device moves linearly and parallel to a Y-axis, as indicated by arrow A, and therefore measurement spot 14 moves linearly along arrow A as well. A camera (not shown) is used to track a selected pattern 15 on wafer 12 as wafer 12 rotates in order to keep track of which point on wafer 12 is actually being examined by spot 14.

As pointed out above, the center of wafer 12 and the center of rotation of stage 10 are typically offset. This occurs even when eccentric placement of wafer 12 on stage 10 is corrected by prior art methods such as pre-alignment by tracking a notch 17 along a rim 16 of wafer 12. As a result, a blind spot 18 is created that cannot be examined by beam spot 14. Furthermore, as wafer 12 rotates continuously or in small increments of angle θ, pattern 15 rotates continuously or in small increments as well. To compensate, the image needs to be rotated either digitally or by rotating the camera. In performing the rotation a Dove prism can be used to rotate the image without distortion. It should be noted, that when the image is rotated by rotating the camera, then the entire prior art mechanism becomes unduly complicated.

Figure 2:
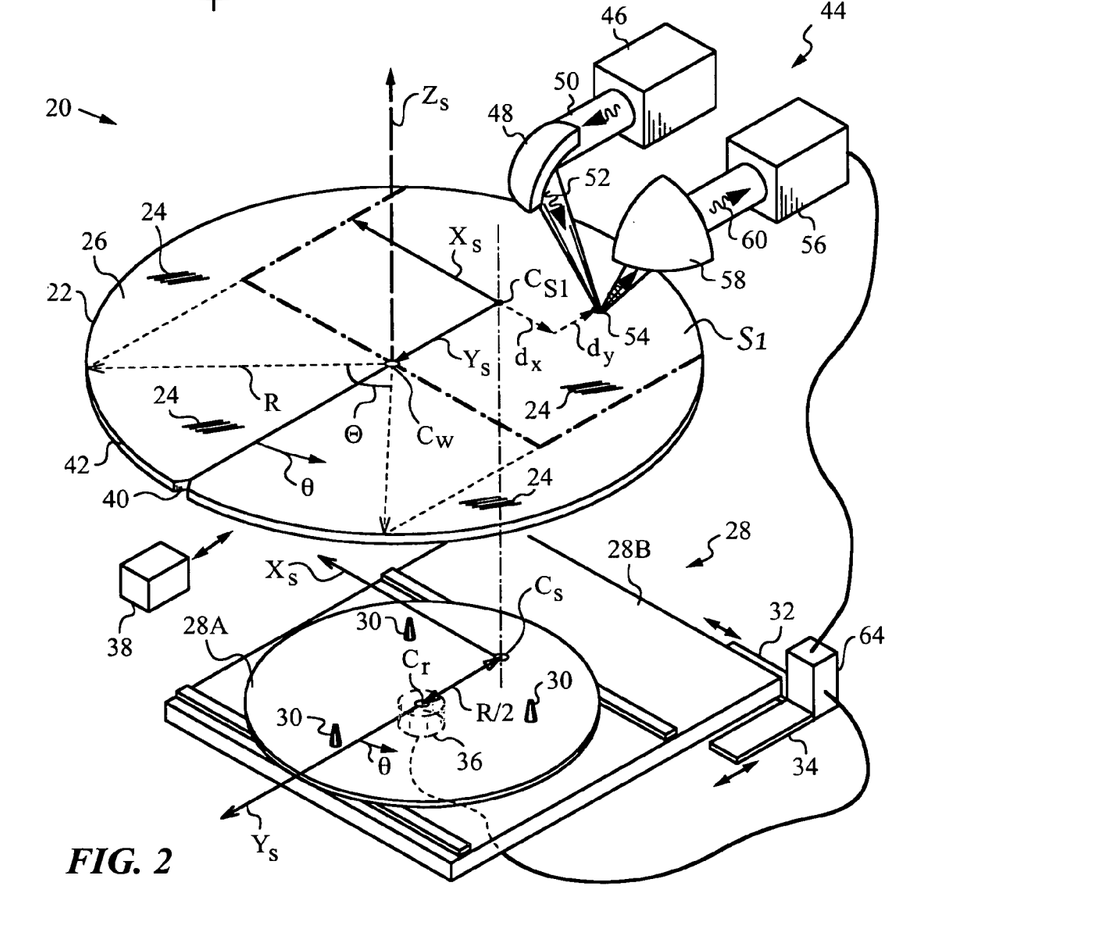
FIG. 2 is a three-dimensional diagram illustrating the basic components and principles of the apparatus and method of invention.

An exemplary apparatus 20 that overcomes the prior art limitations in accordance with the invention is illustrated in FIG. 2. Apparatus 20 is designed for examining features 24 of a sample 22 that is typically disk-shaped and planar, such as a semiconductor wafer. Features 24 are usually small or microscopic, and may include lithographically produced patterns corresponding to circuits, connections and circuit elements. Only a few select features 24 in a greatly magnified format are indicated on a surface 26 of wafer 22 for drawing clarity.

Apparatus 20 has a stage 28 for holding or supporting wafer 22. Stage 28 is a compound stage composed of two individual stages: a theta stage 28A and a linear X-Y stage 28B. Theta stage 28A has a support arrangement in the form of support pins 30 for holding wafer 22. Theta stage 28A sits on top of linear X-Y stage 28B. An X-drive 32 and a Y-drive 34 are provided for moving linear X-Y stage 28B along directions defined along a stage $X_s$ axis and a stage $Y_s$ axis, respectively. Theta stage 28A has a rotary drive or θ-drive 36 for rotating theta stage 28A by angle θ about a center of rotation $C_r$.

Theta stage 28A is mounted on linear stage 28A such that center of rotation $C_r$ lies on $Y_s$ axis of linear X-Y stage 28B. In fact, center of rotation $C_r$ is a distance R/2 from a center $C_s$ of X-Y linear stage 28B along $Y_s$ axis, where R is the radius of wafer 22. The full travel range of linear X-Y stage 28B along $Y_s$ axis is R or ±R/2 centered on $C_s$. The full travel range along $X_s$ axis is 2Rsin(180°/n) or ±Rsin(180°/n) centered on $C_s$, where n is the number of sectors as defined below in reference to FIG. 2.

Wafer 22 is placed on stage 28, and more precisely on support pins 30 of theta stage 28A. The placement is such that a wafer center $C_w$ is substantially aligned with center of rotation $C_r$ and center $C_s$, of an angular sector S1 is aligned with center $C_s$. Any known technique can be used to ensure sufficient alignment. In the present embodiment, a pre-aligner 38 and a notch 40 along a rim 42 of wafer 22 are used to ensure substantial alignment between center of rotation $C_r$ and wafer center $C_w$.

Apparatus 20 has a measurement assembly 44 that is located above wafer 22. Assembly 44 has an illumination source 46 and optics 48 for producing a measurement beam 50 of probe radiation 52 to examine features 24 on wafer 22 optically. Wafer 22 is illuminated with probe radiation 52 focused to a measurement beam spot 54 on surface 26 of wafer 22. Assembly 44 has a detector 56 with optics 58 for collecting and studying a scattered portion 60 of probe radiation 52. Any suitable scatterometry or other optical examination method can be employed in studying scattered portion 60.

The above-described mounting relationship of stages 28A and 28B ensures that center $C_w$ of wafer 22 is offset from center $C_{S1}$ of sector S1 by R/2 and coincident with center $C_r$ of rotation of theta stage 28A. Thus, when measurement assembly 44 is configured such that beam spot 54 is centered on center $C_{S1}$ of sector S1, then entire sector S1 delimited by the dashed and dotted lines can be examined with beam spot 54 by moving linear X-Y stage 28B only. In other words, each location on wafer 22 in sector S1 can be arrived at by a displacement along $X_s$ and a displacement along $Y_s$, as indicated by the two dashed arrows $d_x$, $d_y$. In other words, beam spot 54 can be trained on all points within sector S1 without moving measurement assembly 44 or rotating wafer 22.

In accordance with the invention, this configuration of stages 28A, 28B of apparatus 20 is utilized by a scheduling module 64 for coordinating X-drive 32, Y-drive 34 and θ-drive 36 with measurement assembly 44 such that wafer 22 is examined in an even number n of angular sectors. The angular sectors are defined by a sector angle Θ that is the same for each sector. Specifically, the sector angle Θ is defined in terms of n as follows:

$$\Theta = \frac{360°}{n};$$

where n=4m and m is an integer, such that multiple rotations of sector angle Θ always include angles 90° and 180°. In the present embodiment m=1 and thus n=4 and sector angle Θ is equal to 90°.

Figure 3A:
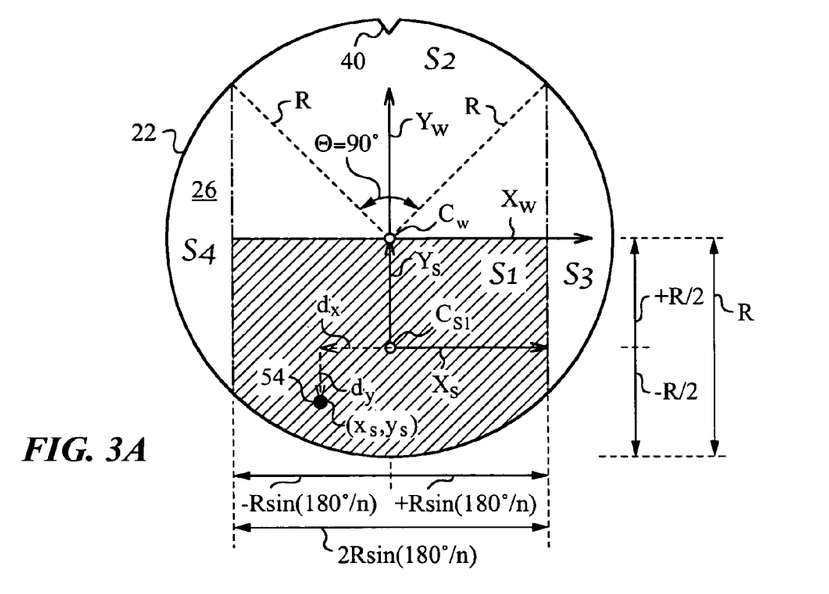
FIG. 3A is a top plan view of a sample subdivided into four (n=4) angular sectors in its canonical (θ=0) orientation.

FIG. 3A is a top plan view of surface 26 of wafer 22 subdivided into four (n=4, m=1) angular sectors S1, S2, S3 and S4 while in its canonical (θ=0) orientation corresponding to the orientation of FIG. 2. In this position sector S1 of wafer 22 is accessible for examination by measurement beam spot 54 originally centered on center $C_{S1}$ of sector S1 of wafer 22. Any location in sector S1 can be accessed without rotating theta stage 28A, but only displacing linear X-Y stage 28B along $X_s$ and $Y_s$ by displacements $d_x$ and $d_y$.

Prior to examination of features 24, the operator performs a pre-alignment procedure with pre-aligner 38 using notch 40 for reference. once pre-alignment is complete, scheduling module 64 coordinates X-drive 32, Y-drive 34 and θ-drive 36 with measurement assembly 44 such that wafer 22 is examined in succession in the four angular sectors S1, S2, S3 and S4. Measurement assembly 44 is positioned such that when X- and Y-drives 32, 34 keep X-Y linear stage 28B in the middle of the corresponding $X_s$ and $Y_s$ travel ranges R, 2Rsin (180°/n), measurement beam spot 54 is incident on center $C_{S1}$ of sector S1 of wafer 22 at an offset R/2 from wafer center $C_w$. When examining successive sectors S2, S3, S4 measurement beam spot 54 is also initially centered on the centers of these sectors.

To commence examination in sector S1, scheduling module 64 instructs θ-drive 36 to rotate wafer 22 into the canonical position (θ=0). In this position notch 40 is aligned along $Y_w$ axis, which in turn is parallel with $Y_s$ axis of stage 28 (see FIG. 2). Once wafer 22 is in the canonical position, module 64 instructs X- and Y-drives 32, 34 to move linear X-Y stage in any suitable manner to cover $X_s$ and $Y_s$ travel ranges R, 2Rsin (180°/n). Since n=4 and m=1, the $X_s$ travel range is equal to 2Rsin(45°) or 1.41R. The movement is performed in a pattern selected such that spot 54 illuminates all features 24 that need to be optically examined by measurement assembly 44. If the entire sector S1 is to be examined, a raster pattern can be used.

Figure 3B:
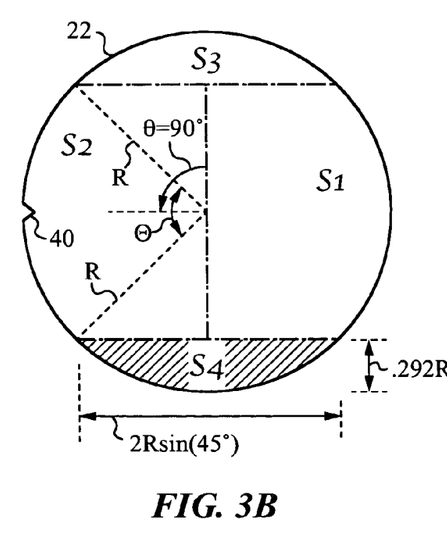
FIG. 3B is a top plan view of the sample of FIG. 3A rotated by one step at one sector angle Θ to the left.

To examine the next sector, module 64 instructs θ-drive 36 to rotate wafer 22 by one sector angle Θ, as shown in FIG. 3B. In this case wafer 22 is rotated to the left. Of course, wafer 22 could also be rotated to the right and/or be rotated by a multiple of sector angle Θ, e.g., by two sector angles 2Θ. In any event, when wafer 22 is rotated, the coordinates on wafer 22 have to be recalculated, since they are no longer coincident with $X_s$ and $Y_s$. For example, one can continue to use wafer coordinates centered at wafer center $C_w$ with the polar axis pointed to notch 40. Starting from the canonical position (when θ=0 and notch 40 is on the positive $Y_s$ axis of X-Y linear stage 28B) the coordinate transformation for any point $x_s$, $y_s$ in stage 28B coordinates $X_s$, $Y_s$ can be described in terms of center offset R/2 and rotation angle θ as:

$$\begin{pmatrix} x_s \\ y_s \end{pmatrix} = \begin{pmatrix} \cos\theta & -\sin\theta \\ \sin\theta & \cos\theta \end{pmatrix} \begin{pmatrix} x_w \\ y_w \end{pmatrix} + \begin{pmatrix} 0 \\ R/2 \end{pmatrix}, \quad \text{Eq. 1}$$

where $x_w$, $y_w$ are the coordinates of the point in wafer coordinates $X_w$, $Y_w$ centered at center $C_w$ of wafer 22. Since in accordance with the method of invention rotation angle θ changes in multiples of sector angle Θ the rotation matrix for the present case of n=4 assumes only 4 different forms, i.e., for θ=0°, 90°, 180°, and 270°. In addition, angle θ does not change during the time a particular sector is being examined. Hence, unlike in the case of the prior art solutions, examination of wafer 22 is not accompanied by continuous or small changes in angle θ (rotations) during measurement and hence avoids the prior art problems outlined above.

Now, when examining sector S4 as shown in FIG. 3B, the travel ranges for linear X-Y stage 28B have to be adjusted. In particular, although $X_s$ remains the same, travel range $Y_s$ decreases to 0.292R (or R-Rsin(45)). In addition, the coordinate transformation of equation 1 has to be used to correlate the position $x_w$, $y_w$ of beam spot 54 on wafer 22 to stage coordinates $x_s$, $y_s$.

Figure 3C:
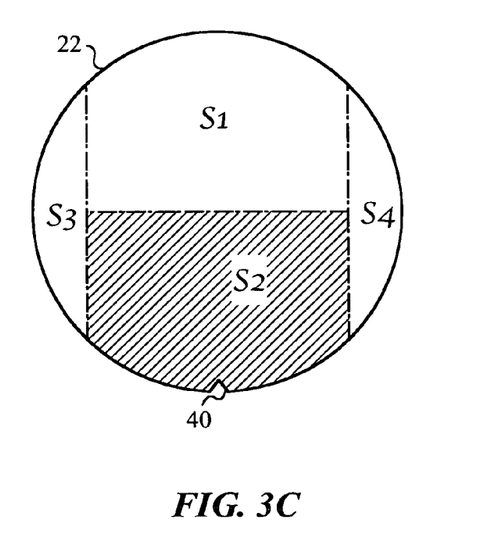
FIG. 3C is a top plan view of the sample of FIG. 3A rotated by two steps of one sector angle Θ to the left.

After sector S4 has been studied, module 64 instructs θ-drive 36 to rotate theta stage 28A by another sector angle Θ to the left. This results in wafer 22 being positioned for examination of sector S2 as shown in FIG. 3C. Then, once again, equation 1 is used to correlate the position $x_w$, $y_w$ of beam spot 54 on wafer 22 to stage coordinates $x_s$, $y_s$ during examination. Finally, module 64 instructs θ-drive 36 to rotate theta stage 28A by still another sector angle Θ to the left to examine sector S4.

Figure 4:
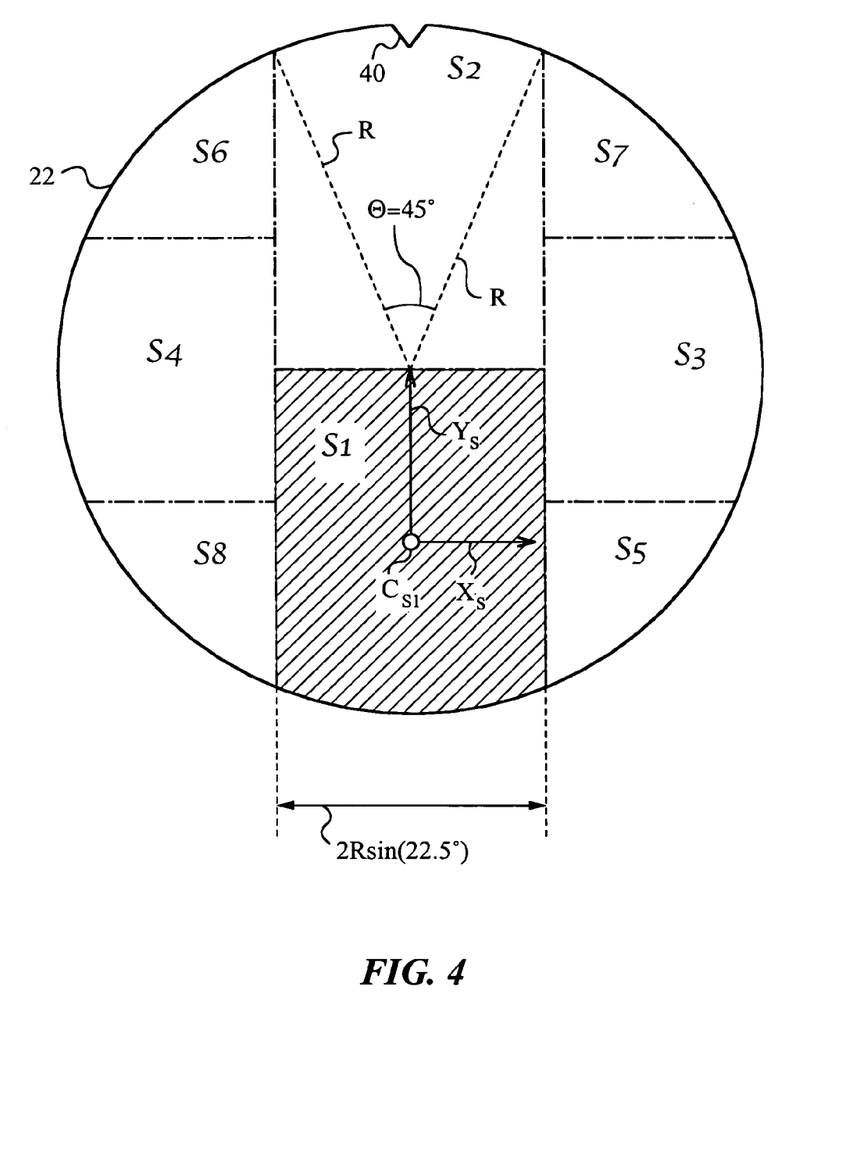
FIG. 4 is a top plan view of a sample subdivided into eight (n=8) angular sectors in its canonical (θ=0) orientation.

The method of invention permits one to subdivide surface 26 of wafer 22 into more than four sectors. For example, FIG. 4 is a top plan view in which wafer 22 is subdivided into eight (n=8, m=2) angular sectors S1, S2, . . . S8. Wafer 22 is shown in its canonical (θ=0) orientation with notch 40 on positive axis $Y_s$. The travel range $X_s$ is 2Rsin(22.5°) or 0.77R and sector angle Θ=45°. In order to examine successive sectors, module 64 instructs θ-drive 36 to rotate theta stage 28A by sector angle Θ=45°. The travel ranges for each sector are summarized in table 1 below.

| Sector | X-range | Y-range | θ |
| --- | --- | --- | --- |
| S1 | −0.383R < x < 0.383R | y < 0 | 0° |
| S2 | −0.383R < x < 0.383R | y > 0 | 180° |
| S3 | x > 0.383R | −0.383R < y < 0.383R | 90° |
| S4 | x < −0.383R | −0.383R < y < 0.383R | −90° |
| S5 | x > 0.383R | y < −0.383R | 45° |
| S6 | x < −0.383R | y > 0.383R | −135° |
| S7 | x > 0.383R | y > 0.383R | 135° |
| S8 | X < −0383R | y < −0.383R | −45° |

Equation 1 is used to transform from stage coordinates $x_s$, $y_s$ to wafer coordinates $x_w$, $y_w$ as before. Finally, theta stage 28A is rotated by −θ and linear X-Y stage is translated by (−$x_s$, −$y_s$) to move point ($x_w$, $y_w$) to beam spot 54. It should be noted that scheduling module 64 can enforce any examination order, including examining diametrically opposite pairs of angular sectors in succession.

To monitor which angular sector is actually being examined stage 28, and in particular θ-drive 36 of theta stage 28A is set up to communicates with scheduling module 64. Specifically, after pre-alignment and initial calibration in the canonical position (θ=0), theta stage 28A keeps track of rotation angle θ executed by θ-drive 36 and communicates it to module 64. Since a small number of θ values are used in the examination process (e.g., 4, 8, 16 etc.), obtaining angle θ from theta stage 28A directly without additional monitoring equipment is a particularly simple and reliable way of monitoring rotation angle θ. The value of θ thus obtained can be used not only for monitoring the rotation of wafer 22 for purposes of measurement or scheduling, but also for displaying any images of wafer 22 to an operator or user.

Figure 5:
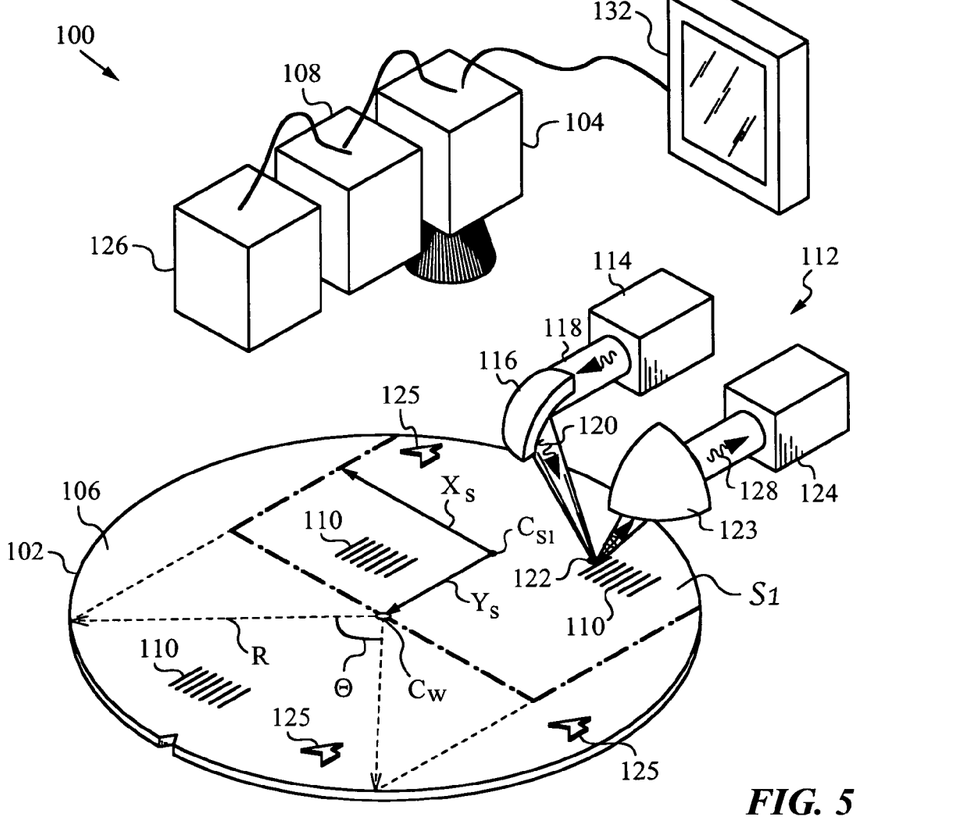
FIG. 5 is a partial three-dimensional view of another apparatus in accordance with the invention.

FIG. 5 shows a partial three-dimensional view of another apparatus 100 for examining a planar disk-shaped sample 102. In this embodiment apparatus 100 is equipped with a viewing mechanism 104 for imaging surface 106 of sample 102 with features 110 that are to be examined. As in the prior example, features 110 are microscopic, and shown in a magnified view in few areas only for reasons of drawing clarity. A measurement assembly 112 is provided for examining features 110.

Assembly 112 has an illumination source 114 and optics 116 for producing a measurement beam 118 of probe radiation 120 to examine features 110 on sample 102 optically. During such examination, sample 102 is illuminated with probe radiation 120 focused to a measurement beam spot 122 on surface 106 of sample 102. Assembly 112 has a detector 124 with optics 123 for collecting and studying a scattered portion 128 of probe radiation 120.

Apparatus 100 has an image rotation module 108 for rotating an image of certain pre-selected reference features 125 captured by mechanism 104. It should be noted that reference features 125 are typically not selected from among features 110 which are to be examined. Rotation module 108 relies on pattern matching of rotated reference features 125 to determine the rotation angle θ. This embodiment is preferred when measurement assembly 112 requires precise calibration for proper measurement and analysis.

Viewing mechanism 104 may use scattered portion 128 of probe radiation 120 in the field of view of assembly 112 to reconstruct and image reference features 125. Alternatively, it can obtain the image independently with separate elements such as additional illumination sources (not shown). In fact, a very wide range of imaging approaches can be employed by mechanism 104, including integrating it with detector 124, as will be appreciated by those skilled in the art.

Image rotation module 108 is in communication with viewing mechanism 104 so that it can receive the image of reference features 125. Module 108 performs a rotation of the image of reference features 125. In conjunction with a pattern matching module 126, module 108 is configured to rotate the image of features 125 by multiple of 180°/n until it matches a certain pattern associated with a given orientation of sample 102. For this purpose, features 125 in particular orientation or orientations may be selected and stored as a stored pattern 127. In selecting features 125 for pattern 127, it is important to make a choice that will permit reliable rotation control. However, since sector angles Θ are generally large even when there are many sectors, e.g., n=16 or more, the rotations performed by θ-drive are still significant enough that matching the rotated image of features 125 to stored pattern 127 is in general not a challenging problem. Thus, direct communication with θ-drive may not be necessary in most applications.

Figure 6A:
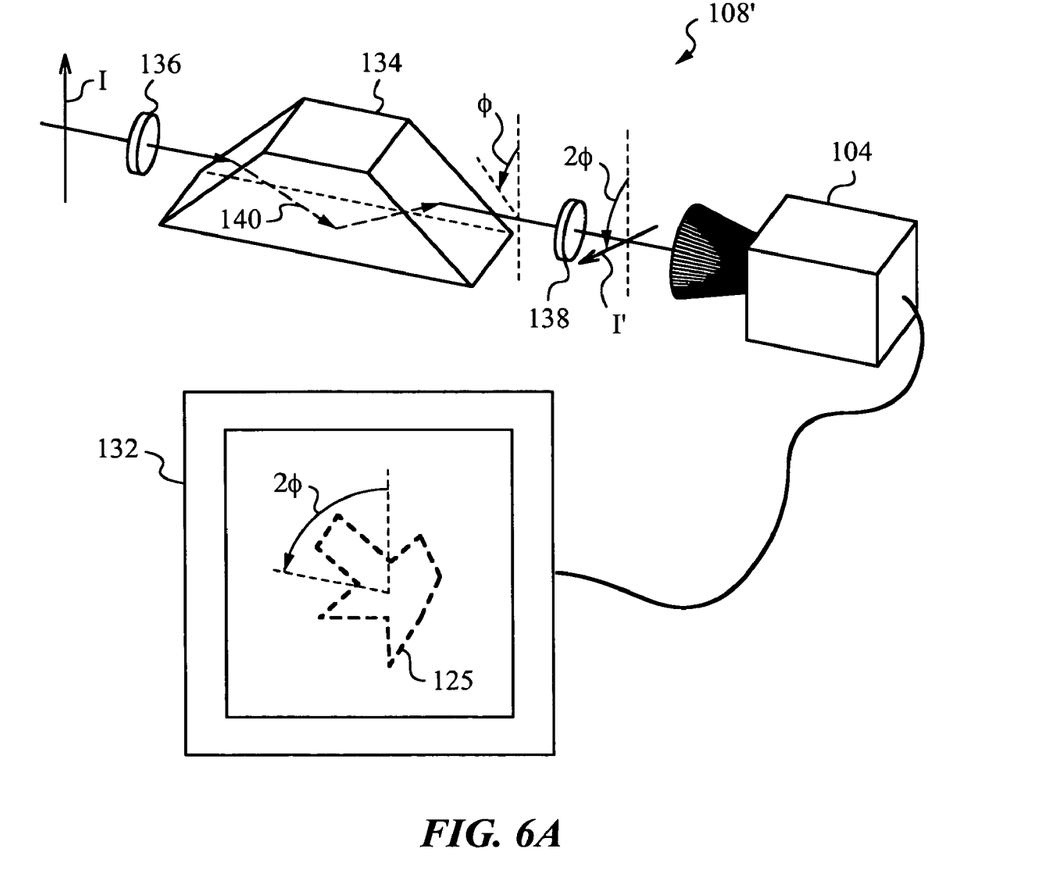
FIG. 6A is a three-dimensional view of a mechanical image rotation module that can be employed in the apparatus of FIG. 5.

Another exemplary image rotation module 108' that can be used by the apparatus of invention is illustrated in the three-dimensional view of FIG. 6A. Unlike module 108, which performs the rotation digitally, rotation module 108' performs the rotation mechanically using a Dove prism 134. To accomplish this, module 108 is positioned before viewing mechanism 104.

Module 108' has a set of lenses 136, 138 positioned before and after Dove prism 134 for focusing the light coming from feature 125 and guiding it through prism 134 to follow a total internal reflection path 140, as shown. In this arrangement, a mechanical rotation of prism 134 about the optical axis by a mechanical rotation angle φ, results in an optical rotation by twice mechanical rotation angle φ, or simply 2φ. The orientation of feature 125 before and after undergoing the rotation is indicated by arrows I and I', respectively. An image of feature 125 rotated by 2φ is shown on display 132.

A person skilled in the art will appreciate that mechanical rotation module 108' admits of a large number of alternative mechanical rotation mechanisms. Also, any number of alternative modules that use no moving parts can be used. For example, rotation modules that employ acousto-optic beam deflectors and polygon mirrors emulating the operation of a Dove prism can be used to avoid the need for mechanical drives and/or moving parts.

Figure 6B:
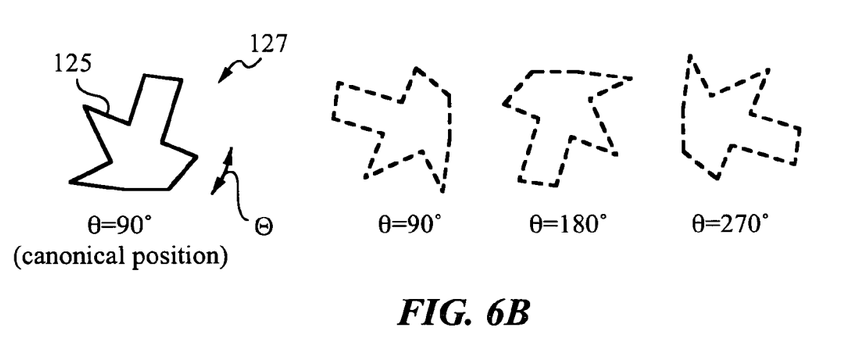
FIG. 6B are diagrams of features stored for use as pattern for pattern matching to determine orientation of the sample.

Irrespective of the type of image rotation module and/or technique, it is important for pattern matching to select one asymmetric reference feature 125 and store it in the form of stored pattern 127 of images at various image rotations as shown in FIG. 6B. Reference feature 125 can be any asymmetric object on the surface of the die, including a fiducial, indicia or any type of markings or points on surface 106 of sample 102. Feature 125 should be selected bearing in mind that pattern 127 should exhibit a certain level of asymmetry and in particular, a sufficient level of asymmetry to distinguish a number of pattern orientations at least equal to the number n of sectors (since the number of sectors is the number of discrete values that θ is allowed to assume). The images of feature 125 at different orientations corresponding to the different permissible values of θ based on the number of angular sectors are thus stored as pattern 127 and then matched to determine actual rotation angle θ.

There are several ways of doing pattern matching and thus finding rotation angle θ. When sample 102 is rotated by an unknown angle θ but with a step of 180°/n, an image is obtained by mechanism 104. This is the current image and we define it as image B. To find rotation angle θ one can then perform any of the following steps:

1. Store an image A of reference feature 125 as a standard image that is collected when θ=0. Rotate image B with a step 180°/n using image rotation module 108 and find the best match to image A using pattern matching module 126. If the best match yields a rotation angle of alpha, it means the sample is rotated by alpha.
2. Use pattern recognition software that matches a rotated image. When using such software, one just needs to try several or all the possible rotation angles θ in pattern matching module 126 and the best match will correspond to the correct rotation angle θ.
3. Store a set of images A0, A1, A2, A3, . . . , A2n-1, of reference feature 125 collected at angles 0°, 180°/n, 2*180°/n, 3*180°/n, . . . , (2n-1)*180°/n. This is done at training time. During the measurement, the current image B will be compared with all stored images Ai, and the best match gives the correct rotation angle θ.
4. Couple θ stage with pattern matching module 126 as is well-known to a person skilled in the art and monitor rotation angle θ.

The pattern matching performed with the aid of image rotation module 108 or 108' and pattern matching module 126 has many uses. In one embodiment, apparatus 100 has a drive feedback that is in communication with pattern matching module 126. Based on matching stored pattern 127, and in particular matching its rotated version with the pattern contained in the image of feature 125 observed by viewing mechanism 104, the drive feedback controls at least one of the drives, i.e., X-drive, Y-drive and θ-drive, but preferably at least the θ-drive. In another embodiment, apparatus 100 has an angular sector identification module that is connected to pattern matching module 126. The identification module identifies the angular sectors based on pattern matching. In this case, the pattern matching module can try several or all possible rotations with 180°/n steps, as described above, and the best pattern match yields the correct rotation angle θ.

In still another embodiment, apparatus 100 has a sample offset correction module that is in communication with pattern matching module 126 and performs offset correction of sample 102 based on the pattern matching. In any of these applications of pattern matching module 126, as well as any other applications thereof, it is advantageous to ensure a corresponding level of asymmetry of the stored pattern to ensure that the requisite angular resolution is obtained. Once the correct rotation angle θ is found, the captured image can be rotated for display to an operator.

In addition to determining rotation angle θ, it is sometimes also important to properly orient measurement assembly 112 with respect to features 110 that are to be examined in any given sector. This is important when features 110 have a preferred orientation, i.e., when they are not isotropic. Examples of such features 110 include gratings and other non-isotropic structures encountered in the manufacture of electronic and photonic circuits. In the embodiment shown, features 110 are gratings and they need to be illuminated by measurement beam 118 from a certain angle of incidence.

Figure 6C:
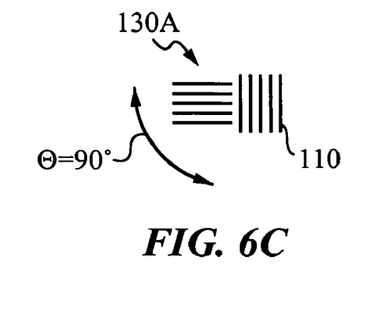
FIGS. 6C-D are diagrams illustrating calibration features for calibrating the measurement process in a particular sector.
Figure 6D:
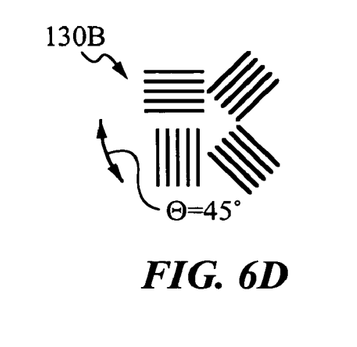

To properly orient measurement assembly 112 a calibration pattern 130 consisting of features 110 is used. FIGS. 6C-D are diagrams illustrating two possible calibration patterns 130A, 130B for calibrating measurement assembly 112. In fact, each sector contains a copy of calibration pattern 130, such that calibration of assembly 112 can be performed independently for measurements that are undertaken in each sector.

Patterns 130A, 130B are composed of features 110 present on sample 102 for calibrating the response of features 110 with respect to the angle of incidence of probe radiation 120. Pattern 130A illustrated in FIG. 6B is designed for embodiments where sample 102 is segmented into four sectors and sector angle Θ=90°. FIG. 6C illustrates a pattern 130B that is optimized for embodiments where sample 102 is segmented into eight sectors and sector angle Θ=45°. Each pattern 130 is guaranteed to provide a calibration portion of features 110 that are parallel (or perpendicular) to actual features 110 that are to be examined in the sector.

Although measurement assembly 112 can be stationary, in order to take best advantage of calibration pattern 130 and achieve proper orientation rapidly, it is preferred that measurement assembly 112 be mobile.

In an alternative embodiment, image rotation module 108 of apparatus 100 can be in communication with the θ-drive of the theta stage (not shown). Thus, module 108 can obtain rotation angle θ from θ-drive directly rather than obtaining it from pattern matching or other process. Given that the number of possible rotation angles θ is small due to small number n, this is an effective way of obtaining rotation angle θ. Furthermore, rotation angle θ obtained from θ-drive can be used for rotating the image of sample 102. Thus, for example, in cases where apparatus 100 is provided with a display module 132, rotation angle θ obtained directly from θ-drive can be used to rotate the image. This image can be used for display to an operator or user, or else for monitoring the rotation of sample 102.

Rotation angle θ obtained from θ-drive can also be used as a cross-check to confirm rotation angle θ obtained in pattern matching. Such cross-check becomes more important with a larger number n, i.e., as the number of angular sectors into which sample 102 is subdivided increases.

Figure 7:
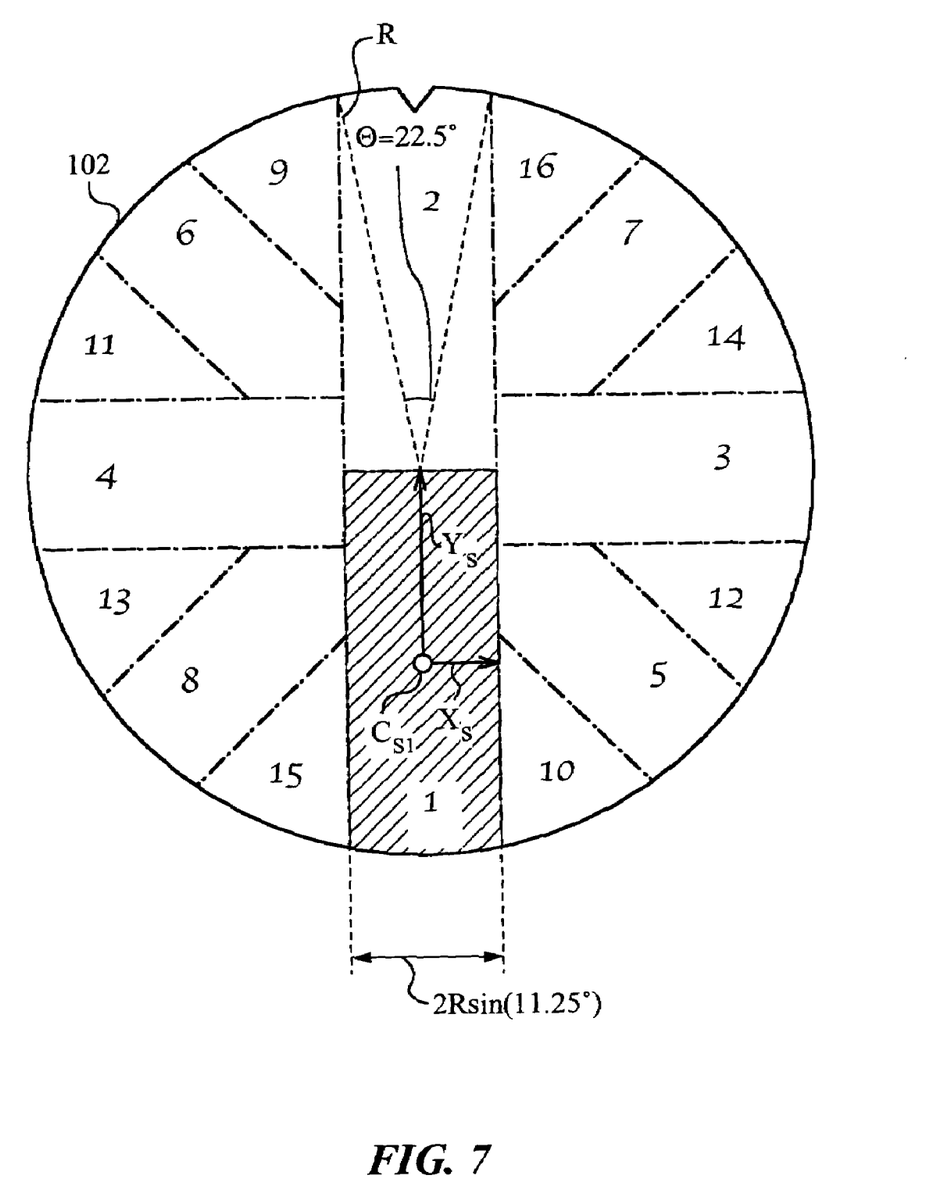
FIG. 7 is a top plan view of a sample subdivided into sixteen (n=16) angular sectors in its canonical (θ=0) orientation.

FIG. 7 illustrates yet another segmentation of sample 102 into n=16 sectors S1, S2, . . . , S16. For clarity, sectors S1, S2, . . . , S16 are merely designated by their sector number. In this embodiment the travel range $X_s$ is equal to 2Rsin(11.25°) or 0.39R and sector angle Θ is 22.5°. In fact, for most applications sector angle Θ is preferably equal to 90°, 45° or 22.5°. Smaller sector angles Θ are also possible, but may not be preferred due to the increased complexity when implementing pattern matching for feedback and control of the drives, sector identification or correction of sample offset.

In any of the above embodiments, or still other embodiments with larger number of sectors, disk-shaped samples can be examined in a small footprint apparatus that is insensitive to misalignments. In particular, the apparatus operates within the footprint of the sample only while still being able to efficiently examine the entire surface of the sample. Further, the apparatus of invention can examine samples such as semiconductor wafers in a configuration that allows the measurement assembly to travel in a very flat and precise manner, whenever such travel is required. In addition, moving reliably between positions in various sectors is very precise and not as costly as in the prior art systems.

In some applications, the θ-drive has a stepper motor for rotating the sample by angular steps that are equal to the sector angle Θ. In one case an encoder with angular feedback can be used to control the position of the angular stepper motor. In another case, a simple DC motor can be used to drive the rotating table, and then any suitable mechanism can be used to enforce such step-wise rotation, including hard stops. The hard stops are used for controlling its angular movement by increments equal to sector angle Θ. In any of these applications the measurement assembly itself can be stationary or mobile.

Figure 8:
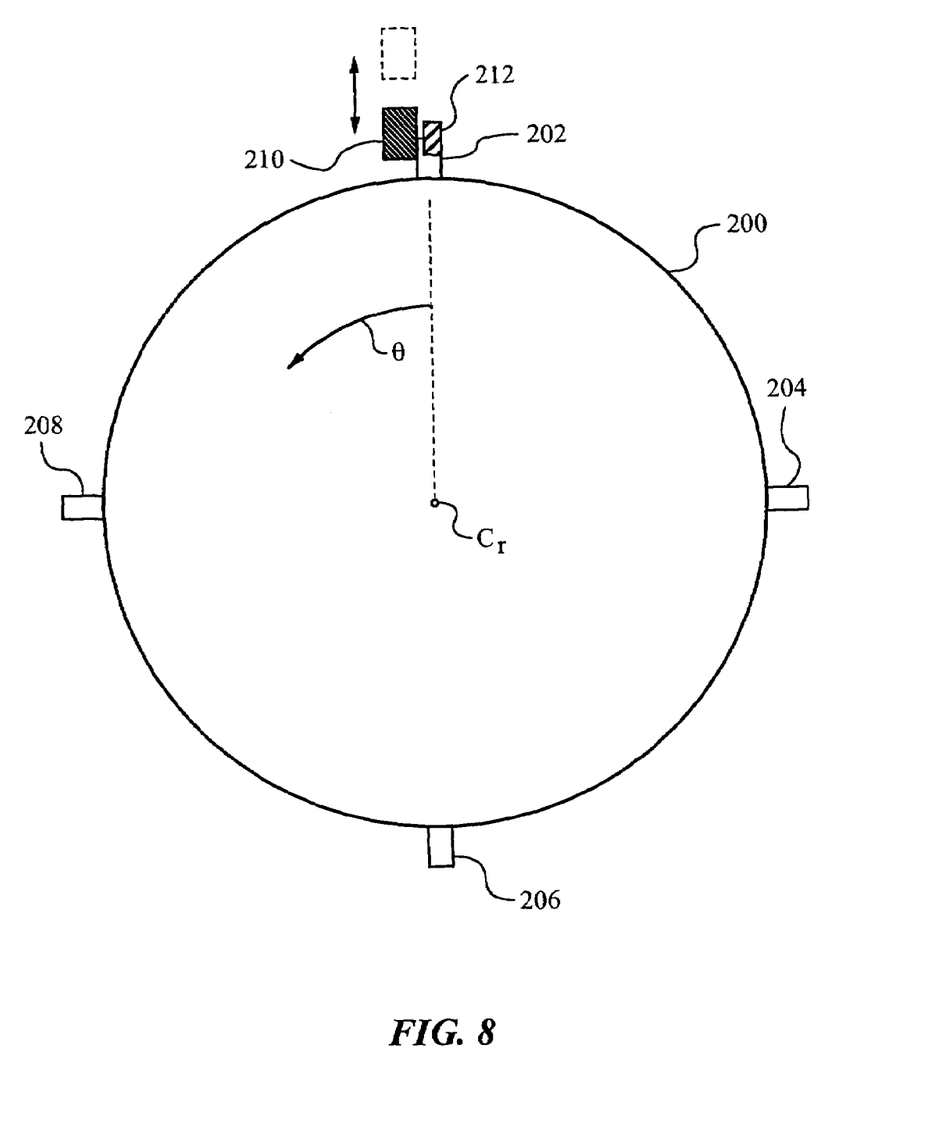
FIG. 8 is a top plan view of a rotary stage that uses hard stops to monitor rotation.

As shown in the top plan view of FIG. 8, a rotary stage 200 can use stepper or servo motors with rotary encoder feedback of the angular position at any given rotation angle θ. There is a closed loop control function used to position to any given θ.

Alternatively, if the θ positions to be measure are known, the rotary table can have adjustable tabs 202, 204, 206, 208 at each position and then a hard stop 210 can be actuated to flip in and out of the tab path. A thru beam sensor 212 can be used to keep track of which pre-determined angular position rotary table 200 is in (in the present case the four permitted angular positions are 0°, 90°, 180° and 270°). In this embodiment a simple motor can be used without encoder feedback and exact position of the rotary table will be known because the actual hard stop and tab will be in contact.

The invention further encompasses a method for examining features of a sample, e.g., a semiconductor wafer that is placed on a stage with three degrees of freedom of motion. Specifically, the method is practiced on a stage with an $X_s$ direction of motion, a $Y_s$ direction of motion and a θ rotation.

The method of invention can be practiced in many variants. In some a specific schedule of examination of the angular sectors can be implemented. For example, the schedule may dictate consecutive examination of diametrically opposite pairs of angular sectors.

Many other embodiments of the apparatus and method are possible. Therefore, the scope of the invention should be judged by the appended claims and their legal equivalents.

We claim:

1. An apparatus for examining features of a disk-shaped sample, said apparatus comprising:
    a) a stage for supporting said sample;
    b) an X-drive for moving said stage along an $X_s$ direction;
    c) a Y-drive for moving said stage along a $Y_s$ direction;
    d) a θ-drive for rotating said stage about a center of rotation substantially aligned with a center of said sample;
    e) a measurement assembly above said sample for examining said features; and
    f) a scheduling module for coordinating said X-drive, said Y-drive and said θ drive and said measurement assembly such that said sample is examined in an even number n of angular sectors defined by a sector angle Θ, where Θ=360°/n, and a multiple of Θ includes 90° and 180°, wherein said disk-shaped sample comprises a reference feature, and said apparatus further comprises:
        i) an image rotation module for rotating an image of said reference feature; and
        ii) a pattern matching module for performing a matching of said image of said reference feature with a stored image of said reference feature.

2. The apparatus of claim 1, wherein said scheduling module is in communication with said θ-drive for obtaining a rotation angle θ from said θ drive.

3. The apparatus of claim 2, further comprising an image rotation module for rotating an image of said disk-shaped sample.

4. The apparatus of claim 3, wherein said image rotation module is in communication with said θ-drive for obtaining a rotation angle θ from said θ-drive for rotating said image.

5. The apparatus of claim 1, further comprising a drive feedback in communication with said pattern matching module, said drive feedback controlling at least one of said X-drive, said Y-drive and said θ drive based on said matching.

6. The apparatus of claim 1, further comprising an angular sector identification module in communication with said pattern matching module, said angular sector identification module identifying one of said angular sector based on said matching.

7. The apparatus of claim 1, further comprising a sample offset correction module in communication with said pattern matching module, said sample offset correction module correcting an offset of said sample based on said matching.

8. The apparatus of claim 1, wherein said reference feature has a predetermined level of asymmetry.

9. The apparatus of claim 1, further comprising a calibration pattern comprising said features for orienting said measurement assembly with respect to said features.

10. The apparatus of claim 1, wherein said θ drive further comprises a stepper for rotating said sample by angular steps equal to said sector angle Θ.

11. The apparatus of claim 10, wherein said stepper comprises hard stops.

12. The apparatus of claim 1, wherein said measurement assembly is stationary.

13. The apparatus of claim 1, wherein said measurement assembly is mobile.

14. The apparatus of claim 13, wherein said measurement assembly further comprises hard stops for controlling the angular movement of said measurement assembly by increments of said sector angle Θ.

15. The apparatus of claim 1, further comprising a display module for displaying an image of said disk-shaped sample.

16. A method for examining features of a disk-shaped sample on a stage, said method comprising:
    a) providing said stage with an $X_s$ direction of motion, a $Y_s$ direction of motion and a θ rotation about a center of rotation;
    b) placing said sample on said stage such that a center of said sample is substantially aligned with said center of rotation;
    c) subdividing said sample into an even number n of angular sectors, each of said angular sectors having a sector angle Θ, where Θ=360°/n and a multiple of Θ includes 90° and 180°;
    d) examining said features with a measurement assembly in accordance with a schedule, whereby said stage is coordinated in said $X_s$ direction, said $Y_s$ direction and said θ rotation to examine said sample by said angular sectors, wherein said disk-shaped sample comprises a reference feature, and said apparatus further comprises:

i) an image rotation module for rotating an image of said reference feature; and ii) a pattern matching module for performing a matching of said image of said reference feature with a stored image of said reference feature.

17. The method of claim 16, wherein said sector angle Θ is selected from the group of angles consisting of 90°, 45° and 22.5°.

18. The method of claim 16, further comprising controlling any of said $X_s$ direction of motion, said $Y_s$ direction of motion and said θ rotation based on said matching.

19. The method of claim 16, further comprising identifying at least one of said angular sectors based on said matching.

20. The method of claim 16, further comprising correcting a sample offset based on said matching.

21. The method of claim 16, further comprising orienting said measurement assembly with respect to a calibration pattern comprising said features.

22. The method of claim 16, further comprising rotating said sample by angular steps equal to said sector angle Θ.

23. The method of claim 16, wherein said schedule comprises consecutively examining diametrically opposite pairs of said angular sectors.

* * * * *